(12) United States Patent
Inoue et al.

(10) Patent No.: US 11,596,745 B2
(45) Date of Patent: Mar. 7, 2023

(54) LIVING CELL TRANSPLANTING TOOL

(71) Applicant: Kitazato Corporation, Fuji (JP)

(72) Inventors: Futoshi Inoue, Fujinomiya (JP); Chie Inaba, Fujinomiya (JP)

(73) Assignee: KITAZATO CORPORATION, Fuji (JP)

( * ) Notice: Subject to any disclaimer, the term of this patent is extended or adjusted under 35 U.S.C. 154(b) by 328 days.

(21) Appl. No.: 16/375,939

(22) Filed: Apr. 5, 2019

(65) Prior Publication Data

US 2019/0231982 A1 Aug. 1, 2019

Related U.S. Application Data

(63) Continuation-in-part of application No. PCT/JP2017/036192, filed on Oct. 4, 2017.

(30) Foreign Application Priority Data

Oct. 6, 2016 (JP) .............................. JP2016-197989

(51) Int. Cl.
*A61M 5/315* (2006.01)
*A61K 35/54* (2015.01)
(Continued)

(52) U.S. Cl.
CPC ............ *A61M 5/315* (2013.01); *A61B 17/425* (2013.01); *A61K 35/54* (2013.01); *A61M 25/00* (2013.01);
(Continued)

(58) Field of Classification Search
CPC .......... A61M 25/0009; A61M 25/0043; A61M 2210/1433; A61M 2025/0681;
(Continued)

(56) References Cited

U.S. PATENT DOCUMENTS 1,922,084 A * 8/1933 Gerow .................. A61M 25/10
604/102.03
2,574,840 A * 11/1951 Pieri ............... A61M 25/09033
604/95.04
(Continued)

FOREIGN PATENT DOCUMENTS

EP 0066488 A1 12/1982
EP 2765182 A1 8/2014
(Continued)

OTHER PUBLICATIONS

The extended European search report of the EP corresponding patent application No. 17858453 dated Apr. 7, 2020.
(Continued)

*Primary Examiner* — Scott J Medway
(74) *Attorney, Agent, or Firm* — Muncy, Geissler, Olds & Lowe, P.C.

(57) ABSTRACT

A living cell transplanting device has a flexible tube capable of accommodating living cells and a cell pushing shaft inserted into the tube. The tube has a lumen penetrating therethrough and a reduced diameter front end open portion. The shaft has a small diameter end portion having a diameter smaller than that of the reduced diameter front end open portion and an enlarged diameter portion having an outer diameter larger than an inner diameter of reduced diameter front end open portion. Owing to contact between the enlarged diameter portion of the shaft and the reduced diameter front end open portion of the tube, a progress of the shaft is regulated. By pushing the shaft into the tube after the contact between the enlarged diameter portion and the reduced diameter front end open portion finishes, the enlarged diameter portion of the shaft passes through said reduced diameter front end open portion with expanding the reduced diameter front end open portion of the tube and
(Continued)

projects beyond the reduced diameter front end open portion of the tube.

9 Claims, 15 Drawing Sheets

(51) Int. Cl.
*A61B 17/425* (2006.01)
*A61M 25/00* (2006.01)

(52) U.S. Cl.
CPC . *A61M 2202/09* (2013.01); *A61M 2210/1425* (2013.01)

(58) Field of Classification Search
CPC ........ A61M 25/01; A61M 5/00; A61M 31/00; A61M 2025/0175; A61M 25/0068; A61M 25/0102; A61M 25/007; A61B 17/42; A61B 17/435; A61B 2017/4216; A61B 10/0291; A61B 17/43; A61B 17/425; A61D 19/00; A61D 19/02; A61D 19/04
See application file for complete search history.

(56) References Cited

U.S. PATENT DOCUMENTS

| | | | |
|---|---|---|---|
| 3,256,884 A | | 6/1966 | Hill et al. |
| D208,838 S | * | 10/1967 | St. Amand .................... D24/112 |
| 3,877,430 A | | 4/1975 | Wieder |
| 3,965,901 A | * | 6/1976 | Penny ...................... A61M 1/84 604/119 |
| 4,030,481 A | * | 6/1977 | Hill ........................ A61B 5/037 600/561 |
| 4,173,227 A | | 11/1979 | Cassou |
| 4,661,094 A | * | 4/1987 | Simpson ................ A61B 17/22 604/8 |
| 4,662,381 A | * | 5/1987 | Inaba ................ A61B 10/0291 600/569 |
| 4,790,814 A | * | 12/1988 | Fischl .................... A61B 17/43 600/35 |
| 4,863,441 A | * | 9/1989 | Lindsay ................ A61M 25/00 604/523 |
| 5,147,315 A | * | 9/1992 | Weber ..................... A61B 17/43 600/35 |
| 5,171,218 A | * | 12/1992 | Fonger .............. A61M 25/0606 604/164.02 |
| 5,190,552 A | * | 3/1993 | Kelman .................. A61F 2/167 606/107 |
| 5,195,979 A | * | 3/1993 | Schinkel .................. A61B 1/32 604/164.09 |
| 5,273,527 A | * | 12/1993 | Schatz ............... A61B 10/0291 604/164.13 |
| 5,403,291 A | * | 4/1995 | Abrahamson ....... A61M 25/007 600/435 |
| 5,472,419 A | * | 12/1995 | Bacich .............. A61M 25/0068 604/515 |
| 5,667,489 A | * | 9/1997 | Kraff .................... A61F 9/00745 604/35 |
| 5,725,495 A | * | 3/1998 | Strukel ................. A61M 1/743 604/44 |
| 5,997,487 A | * | 12/1999 | Kolehmainen ... A61M 25/0009 600/585 |
| 6,280,423 B1 | | 8/2001 | Davey ............. A61M 25/0029 604/525 |
| 6,605,093 B1 | * | 8/2003 | Blake .................... A61F 2/1664 606/107 |
| 6,740,049 B2 | * | 5/2004 | Wallach ............. A61B 10/0291 600/569 |
| 6,858,033 B2 | * | 2/2005 | Kobayashi ............ A61F 2/1678 623/6.11 |
| 7,637,904 B2 | * | 12/2009 | Wingler ................ A61B 17/43 604/533 |
| 7,695,492 B1 | * | 4/2010 | Ashby ................ A61B 17/0057 606/213 |
| 8,114,047 B2 | * | 2/2012 | Sakai ................ A61M 25/0068 604/30 |
| 8,292,841 B2 | * | 10/2012 | Gregersen ........... A61M 1/3661 604/29 |
| 8,545,434 B2 | * | 10/2013 | Bosel .................. A61M 25/003 604/43 |
| 9,155,862 B2 | * | 10/2015 | Bellisario ........... A61M 25/007 |
| 9,168,355 B2 | * | 10/2015 | Braga ................ A61M 25/007 |
| D748,252 S | * | 1/2016 | King .......................... D24/130 |
| 9,399,112 B2 | * | 7/2016 | Shevgoor ................ A61M 5/14 |
| 10,130,269 B2 | * | 11/2018 | McCaffrey ............ A61M 25/00 |
| 10,918,474 B2 | * | 2/2021 | Liou ....................... A61F 2/148 |
| 2003/0078537 A1 | * | 4/2003 | Jang .................... A61M 25/104 604/96.01 |
| 2004/0006318 A1 | * | 1/2004 | Periakaruppan .... A61M 25/007 264/145 |
| 2004/0064128 A1 | * | 4/2004 | Raijman ........... A61M 25/0021 604/523 |
| 2005/0137448 A1 | | 6/2005 | Wingler et al. |
| 2005/0261703 A1 | * | 11/2005 | Feingold ................ A61F 2/1678 606/107 |
| 2006/0020259 A1 | * | 1/2006 | Baumeister ............. A61F 9/009 606/107 |
| 2006/0142703 A1 | * | 6/2006 | Carter ................ A61M 25/0052 604/264 |
| 2006/0173539 A1 | * | 8/2006 | Shiuey ..................... A61F 2/145 623/5.11 |
| 2006/0184181 A1 | * | 8/2006 | Cole ...................... A61F 2/1662 606/107 |
| 2006/0287610 A1 | * | 12/2006 | Wiegerinck ........ A61B 10/0096 600/563 |
| 2007/0050023 A1 | * | 3/2007 | Bessiere ............... A61F 2/1691 623/6.12 |
| 2007/0129704 A1 | * | 6/2007 | O'Mahony ....... A61M 25/0029 604/508 |
| 2007/0191810 A1 | * | 8/2007 | Kennedy ........... A61M 25/0015 604/508 |
| 2007/0208422 A1 | * | 9/2007 | Walter .................... A61F 9/007 623/5.11 |
| 2007/0244559 A1 | * | 10/2007 | Shiuey ..................... A61F 9/007 623/5.11 |
| 2007/0255230 A1 | * | 11/2007 | Gross ................. A61B 17/8811 604/272 |
| 2008/0082080 A1 | * | 4/2008 | Braga ................ A61M 1/3661 604/523 |
| 2008/0243156 A1 | * | 10/2008 | John ....................... A61F 2/142 606/166 |
| 2008/0255578 A1 | * | 10/2008 | Neusidl ................. A61F 9/0017 606/107 |
| 2008/0269769 A1 | * | 10/2008 | Dybbs ................. A61F 9/0133 606/166 |
| 2008/0269771 A1 | * | 10/2008 | Fulcher ................... A61F 9/007 606/107 |
| 2008/0281341 A1 | * | 11/2008 | Miller ..................... A61F 9/007 606/166 |
| 2009/0118661 A1 | * | 5/2009 | Moehle ................ A61M 1/3659 604/6.16 |
| 2013/0053763 A1 | * | 2/2013 | Makino ................ A61M 25/003 604/523 |
| 2013/0138053 A1 | * | 5/2013 | Shippert ................ A61M 1/84 604/272 |
| 2013/0178790 A1 | * | 7/2013 | Tekulve ................ A61B 17/22 604/28 |
| 2013/0310767 A1 | * | 11/2013 | Solar .................... A61M 39/22 604/247 |
| 2014/0148651 A1 | * | 5/2014 | Aman .................... A61M 29/02 600/207 |
| 2014/0234956 A1 | | 8/2014 | Inoue |
| 2015/0045769 A1 | * | 2/2015 | Cabrera Aquino ..... A61M 5/46 604/506 |
| 2016/0262734 A1 | * | 9/2016 | Chin-Ly ............... A61B 10/04 |
| 2016/0339206 A1 | * | 11/2016 | Cunningham .... A61M 25/0041 |
| 2017/0290605 A1 | * | 10/2017 | Bakri ................. A61M 25/0026 |
| 2018/0360494 A1 | * | 12/2018 | Melsheimer ....... A61M 25/0102 |

(56) References Cited

U.S. PATENT DOCUMENTS

| | | | |
|---|---|---|---|
| 2018/0369538 A1* | 12/2018 | Lee | A61L 29/146 |
| 2020/0054861 A1* | 2/2020 | Korkuch | A61M 60/268 |
| 2020/0061337 A1* | 2/2020 | Singh | A61M 25/007 |
| 2020/0261707 A1* | 8/2020 | Shikhman | A61B 18/06 |

FOREIGN PATENT DOCUMENTS

| | | |
|---|---|---|
| ES | 2207378 A1 | 5/2004 |
| JP | 2004129789 A | 4/2004 |

OTHER PUBLICATIONS

Kazuhiro Kawamura, "Infertility treatment based on Hippo signaling pathway", Journal of Clinical and Experimental Medicine, Nov. 1, 2014 (Nov. 1, 2014), vol. 251, No. 5, pp. 462 to 466 (Cited in the ISR of PCT/JP2017/036192 which is disclosed herein, therefore, it is believed concise explanation of the relevance has been given).

English translation of International Search Report of PCT/JP2017/036192 dated Nov. 14, 2017.

English translation of Written Opinion of the International Searching Authority of PCT/JP2017/036192 dated Nov. 14, 2017.

* cited by examiner

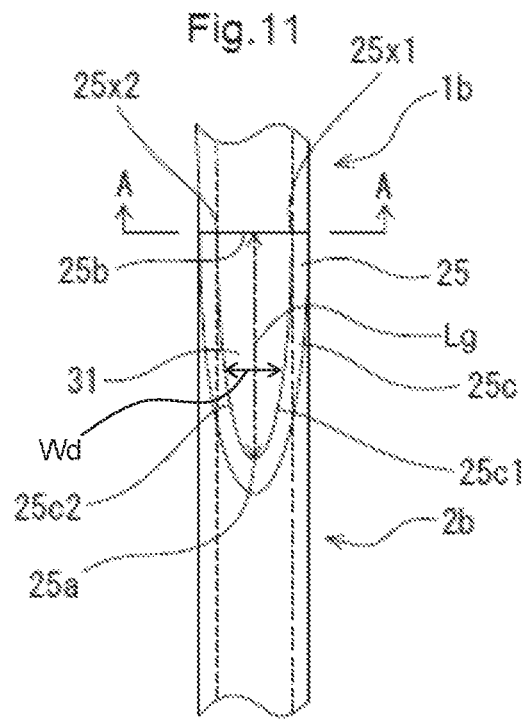
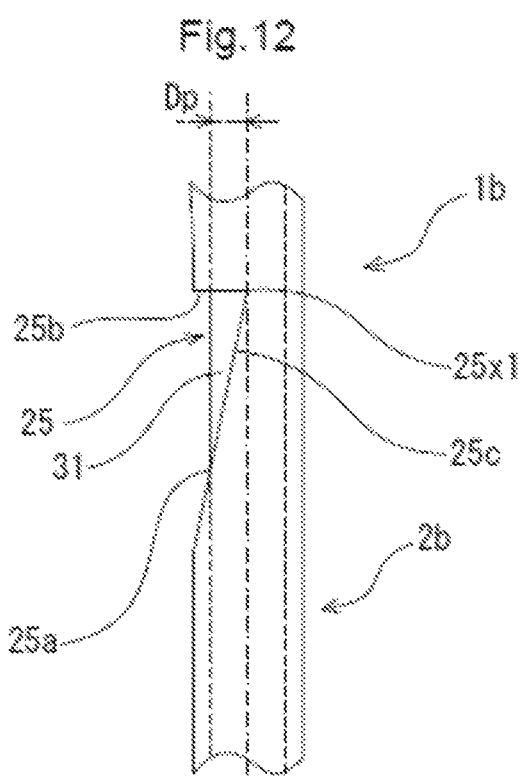

LIVING CELL TRANSPLANTING TOOL

CROSS REFERENCE TO RELATED APPLICATIONS

This U.S. Continuation-In-Part Application claims priority of International Application No. PCT/JP2017/036192 filed Oct. 4, 2017 and Japanese Application No. 2016-197989 filed Oct. 6, 2016, and the entire contents of which are hereby incorporated by reference.

TECHNICAL FIELD

The present invention relates to a living cell transplanting device for transplanting living cells into a living body. More specifically, the present invention relates to a transplanting device for transplanting living cells which are small fragments of an ovary (or ovarian cortex) to a portion disposed between the serosa of the uterine tube and the uterine tube, namely, a device for transplanting ovary tissues to beneath serosa of uterine tube.

BACKGROUND ART

Primordial follicles which are the sources of the ova exist in the ovary. The number of the primordial follicles reaches the peak in the prenatal period and does not increase after they are born, but decreases with age. With the outbreak of menstrual discharge, about 1,000 primordial follicles are activated from a dormant state every month and start to grow and continue to grow under the influence of the factor produced at the locals of the ovary and the endocrine action of the gonadotropin secreted from the pituitary, thus ovulating. When the number of the primordial follicles remaining inside the ovary becomes not more than about 1,000, periodical activation of the ovarian follicles does not occur, with the result that the estrogen excreted from the granulosa cells of the grown ovarian follicles becomes deficient and that menopausal symptom and amenorrhea occurs owing to growth failure of an endometrium. Thus, at the same time, ovulation does not occur, and menopause occurs.

A disease in which the number of ovarian follicles in the ovary rapidly decreases, the number of remaining ovarian follicles becomes not more than a limit value (not more than about 1,000) at the age of less than 40, and menopause occurs is called premature ovarian insufficiency (POI; primary ovarian insufficiency). The premature ovarian insufficiency occurs naturally in one out of 100 women. As the cause of the occurrence of the primary ovarian insufficiency, the abnormality of chromosome and gene, an autoimmune disease, and an iatrogenic disease (ovarian surgery, chemotherapy, and radiation therapy) are known. But the causes for many of the primary ovarian insufficiency are unknown. An effective treatment method for the primary ovarian insufficiency is embryo transplanting of in-vitro fertilization to be carried out by using donated ova (donor ova). It is very difficult for women having the premature ovarian insufficiency to become pregnant with her ova. But in Japan, in-vitro fertilization to be carried out by using the donated ova has not spread. As a reason for that, it is conceivable that women having the primary ovarian insufficiency have a strong feeling of becoming pregnant not with other woman's ova, but with her own ova. Although the donation of ova is not prohibited in Japan, there is a rule that ova should be provided free of charge. Further, it is risky to collect ova by stimulating the ovary. Furthermore, a donor is required to undergo ova collection treatment. Thus, there are very few ova donors.

An artificial activation remedy (IVA: in-vitro activation) for dormant primordial follicles proposed by Mr. Kawamura and other groups is effective for the primary ovarian insufficiency. It is conceivable that clinical application of the artificial activation remedy will make progress in the future.

The following procedures are performed in the artificial activation remedy for the dormant primordial follicles:

1) Laparoscopic ovariectomy
2) Freezing of ovarian tissue and inspection of remaining ovarian follicles
3) Culturing of ovarian tissue: After a thawed ovarian cortex is broken into a cubic shape or a rectangular shape having a dimension of 1 to 2 mm, an ovarian tissue is cultured for 48 hours by using a PTEN inhibitor and a P13K activator to activate a P13K-Akt signal.
4) Autologous transplantation of ovary: After the culturing of the ovarian tissue, the ovarian tissue is sufficiently cleaned. Thereafter autologous transplantation of the ovary is laparoscopically performed. A patient who has developed the primary ovarian insufficiency has a poor blood flow in the patient's ovary. Thus, conceivably, it is difficult to engraft the transplant ovary in the patient's ovary. Thus, the transplantation of the ovary to the serosa of the ovary rich in the blood flow, easy to be observed by transvaginal ultrasound and facilitates an ovary collection procedure is selected.
5) Monitor for examining growth of ovarian follicles and embryo transplanting of in-vitro fertilization: after the autologous transplantation of the ovary finishes, the patient is subjected to a hormone test (LH, FSH, E2) and transvaginal ultrasound to examine the growth of the ovarian follicles every two weeks. In a case where the ovarian follicles have grown, an ovum is collected as in the case of normal in-vitro fertilization. In a case where a mature ovum is obtained, the ovum is fertilized with a sperm by insemination or micro-insemination. Thereafter, temporarily, the embryo is cryopreserved by a vitrification method. Withdrawal bleeding is caused to perform transplanting of the thawed embryo in a hormone supplementation period.

SUMMARY OF THE INVENTION

Problem to be Solved by the Invention

The artificial activation remedy for the dormant primordial follicles is a new procedure. Thus, to perform this procedure, it is important to perform the autologous transplantation of the ovary. More specifically, it is important to successfully transplant living cells which are fragments of the ovary (or ovarian cortex) to the portion disposed between the serosa of the uterine tube and the uterine tube.

It is an object of the present invention to provide a living cell transplanting device capable of successfully transplanting living cells which are small fragments of an ovary (or ovarian cortex) to a portion disposed between a serosa of a uterine tube and the uterine tube.

Means for Solving the Problems

A living cell transplanting device which achieves the above-described object has the following construction:

The living cell transplanting device comprises a flexible tube capable of accommodating living cells and a cell pushing shaft slidably inserted into said flexible tube;

wherein said flexible tube has a lumen penetrating therethrough from a front end thereof to a rear end thereof and a reduced diameter front end open portion;

said cell pushing shaft has a small diameter end portion having an outer diameter smaller than an inner diameter of said reduced diameter front end open portion of said flexible tube and an enlarged diameter portion having an outer diameter larger than said outer diameter of said small diameter end portion and said inner diameter of said reduced diameter front end open portion and a little smaller than an inner diameter of said flexible tube, wherein a front end of said enlarged diameter portion is close to said small diameter end portion and located at a position rearward from said small diameter end portion; and owing to contact between said enlarged diameter portion of said cell pushing shaft and said reduced diameter front end open portion of said flexible tube, a progress of said cell pushing shaft inserted into said flexible tube is regulated; and by pushing said cell pushing shaft into said flexible tube after said contact between said enlarged diameter portion and said reduced diameter front end open portion finishes, said enlarged diameter portion of said shaft passes through said reduced diameter front end open portion with expanding said reduced diameter front end open portion of said tube and is capable of projecting beyond said reduced diameter front end open portion of said flexible tube.

BRIEF DESCRIPTION OF THE DRAWINGS

FIG. 11 is an enlarged front view of the vicinity of a side opening of the living cell transplanting device of the present invention shown in FIG. 10.

FIG. 12 is an enlarged right side view of the vicinity of the side opening of the living cell transplanting device of the present invention shown in FIG. 10.

MODE FOR CARRYING OUT THE INVENTION

Figure 1:
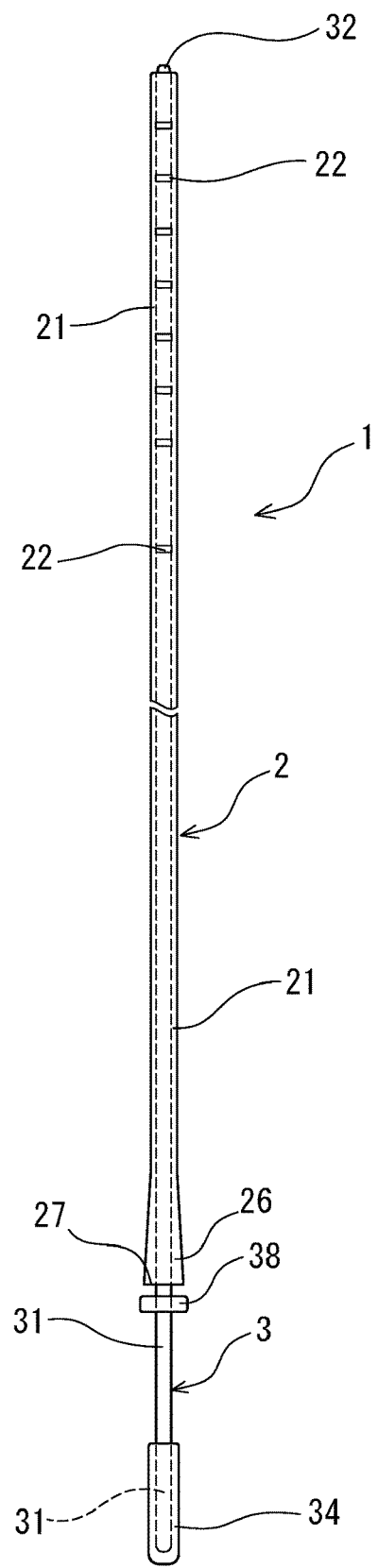
FIG. 1 is a front view of a living cell transplanting device of an embodiment of the present invention.

A living cell transplanting device of the present invention is described below with reference to embodiments shown in the drawings.

A living cell transplanting device 1 of the present invention has a flexible tube 2 capable of accommodating living cells 12 and a cell pushing shaft 3 slidably inserted into the flexible tube 2. The flexible tube 2 has a lumen 24 penetrating therethrough from a front end thereof to a rear end thereof and a reduced diameter front end open portion 23. The cell pushing shaft 3 has a small diameter end portion 32 having a diameter smaller than that of the reduced diameter front end open portion 23 of the flexible tube 2 and an enlarged diameter portion 33 having an outer diameter larger than that of the small diameter end portion 32 and an inner diameter of the reduced diameter front end open portion 23 and a little smaller than an inner diameter of the flexible tube 2. A front end of the enlarged diameter portion 33 is close to the small diameter end portion 32 and located at a position rearward from the small diameter end portion 32. Owing to contact between the enlarged diameter portion 33 of the cell pushing shaft 3 and the reduced diameter front end open portion 23 of the flexible tube 2, the progress of the cell pushing shaft 3 inserted into the flexible tube 2 is regulated. By pushing the cell pushing shaft 3 into the flexible tube after the contact between the enlarged diameter portion 33 and the reduced diameter front end open portion 23 finishes, the enlarged diameter portion 33 passes through the reduced diameter front end open portion 23 with expanding the reduced diameter front end open portion 23 of the flexible tube 2 and is capable of projecting beyond the reduced diameter front end open portion 23 of the flexible tube 2.

The reduced diameter front end open portion 23 of the flexible tube 2 can contact with the enlarged diameter portion 33 of the shaft 3. The reduced diameter front end open portion 23 prevents forward movement of the shaft 3 after contacting the reduced diameter front end open portion 23 of the flexible tube 2 and the enlarged diameter portion 33 of the shaft 3.

After contacting the reduced diameter front end open portion 23 of the flexible tube 2 and the enlarged diameter portion 33 of the shaft 3, the reduced diameter front end open portion 23 of the flexible tube 2 can be expanded by pressing the cell pushing shaft 3. The expanded reduced diameter front end open portion 23 allows a front portion of the cell pushing shaft 3 to pass.

The living cell transplanting device 1 shown in the drawings is for simultaneously transplanting a large number of small fragments of a living tissue to a portion to which the small fragments are to be transplanted. The living cell transplanting device 1 shown in the drawings is an embodiment of the present invention applied to a device for transplanting ovary tissues to beneath serosa of uterine tube, which is effective for simultaneously transplanting a large number of small fragments of an ovary to a portion between the serosa of the uterine tube and the uterine tube.

The living cell transplanting device (device for transplanting ovary tissues to beneath serosa of uterine tube) 1 of this embodiment has the flexible tube 2 capable of accommodating the living cells 12 therein and the cell pushing shaft 3 slidably inserted into the flexible tube 2.

Figure 2:
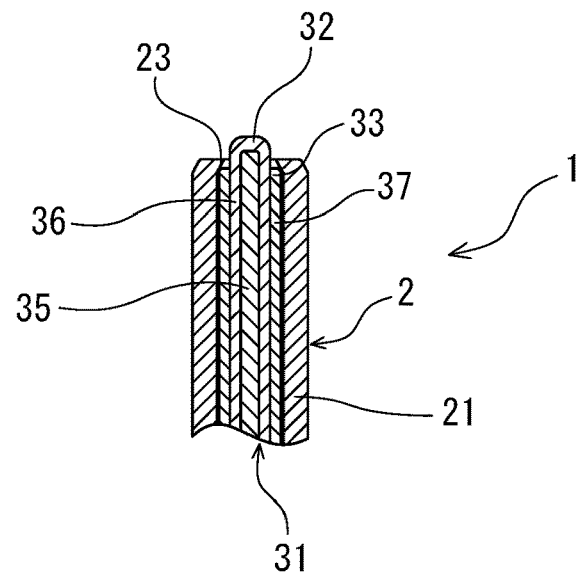
FIG. 2 is an enlarged longitudinal sectional view of a front end portion of the living cell transplanting device shown in FIG. 1.
Figure 3:
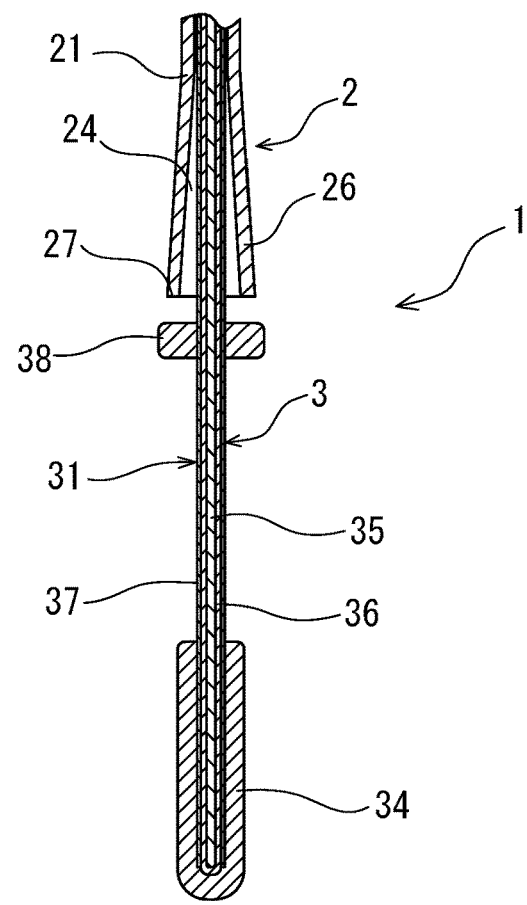
FIG. 3 is an enlarged longitudinal sectional view of a proximal part of the living cell transplanting device shown in FIG. 1.
Figure 4:
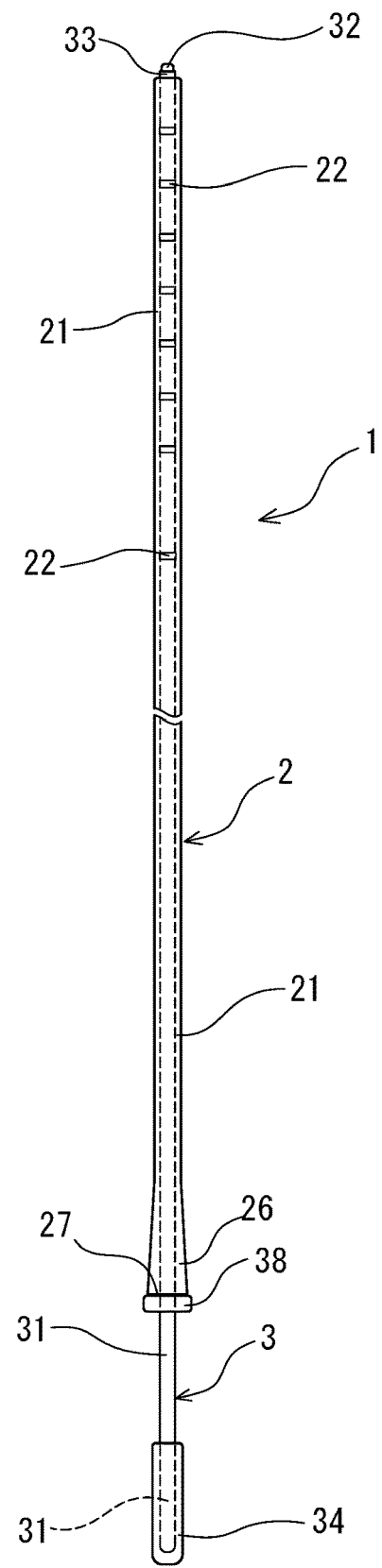
FIG. 4 is an explanatory drawing for explaining the action of the living cell transplanting device shown in FIG. 1.

As shown in FIGS. 1 through 3, the flexible tube 2 has a tube body 21, the reduced diameter front end open portion 23 formed at the front end of the tube body 21, and a tapered enlarged diameter portion 26 formed at a rear end portion of the tube body 21. The flexible tube 2 has the lumen 24 penetrating there through from its front end (reduced diameter front end open portion 23) to rear end (rear end 27 of tapered enlarged diameter portion 26).

The length of the flexible tube is 50 to 300 mm and preferably 100 to 250 mm. The outer diameter of the flexible tube is 1 to 5 mm and preferably 1.5 to 3.5 mm. The inner diameter of the flexible tube is 0.8 to 4.8 mm and preferably 1.3 to 3.3 mm. It is preferable that materials for forming the flexible tube has shape retainability to some extent. As the materials for forming the flexible tube, it is possible to use polyester, polyolefin (for example, polyethylene, polypropylene, ethylene-propylene copolymer), polyamide (for example, nylon 6, nylon 66), polyester (for example, polyethylene terephthalate), and fluororesin (for example, PTFE, ETFE). As shown in FIG. 1, it is preferable to attach a plurality of insertion depth confirming markers 22 on an outer surface of the tube 2.

At least an inner diameter of the reduced diameter front end open portion 23 is set smaller than that of the other part (part rearward from the reduced diameter front end open portion 23) of the flexible tube 2. In the living cell transplanting device 1 of this embodiment, the inner diameter of the front end of the tube 2 is set gradually smaller in a tapered shape toward the front end thereof. By shaping the front end portion of the tube in this way, the enlarged diameter portion of the shaft 3 is capable of easily passing the reduced diameter front end open portion 23 when the cell pushing shaft 3 is pushed into the flexible tube 2. The inner diameter of the reduced diameter front end open portion 23 is set to favorably 65/100 to 95/100 and especially favorably 70/100 to 90/100 of the inner diameter of the part of the tube 2 rearward from the reduced diameter front end open portion 23.

In the living cell transplanting device 1 of this embodiment, an outer diameter of the front end portion of the tube 2 is also set gradually smaller in a tapered shape toward the front end thereof. Therefore, it is easy to insert the front end portion of the tube into a portion to which the small fragments of the living tissue are to be transplanted. It is preferable to set the length of a tapered reduced diameter portion of the tube to 1 to 10 mm and especially preferable to set the length thereof to 2 to 7 mm.

Inner and outer diameters of the tapered enlarged diameter portion 26 are set larger than those of other part (part forward from the tapered enlarged diameter portion 26) of the flexible tube 2. The outer diameter of the tapered enlarged diameter portion 26 is set to favorably 1.1 to 1.5 times and especially favorably 1.2 to 1.4 times longer than that of a part of the tube 2 forward from the tapered enlarged diameter portion 26. It is preferable to set the length of the tapered enlarged diameter portion 26 to 5 to 50 mm and especially preferable to set its length to 10 to 40 mm.

The cell pushing shaft 3 has a small diameter end portion 32 having an outer diameter smaller than an inner diameter of the reduced diameter front end open portion 23 of the flexible tube 2. The cell pushing shaft 3 has an enlarged diameter portion 33 having an outer diameter larger than the outer diameter of the small diameter end portion 32. The outer diameter of the enlarged diameter portion 33 is larger than the inner diameter of the reduced diameter front end open portion 23 and a little smaller than an inner diameter of the flexible tube 2. A front end of the enlarged diameter portion 33 is close to the small diameter end portion 32 and located at a position rearward from the small diameter end portion 32. Specifically, the distance between the front end of the small diameter end portion 32 and that of the enlarged diameter portion 33 is set to preferably 0.2 to 10 mm and especially preferably 0.5 to 5 mm.

As shown in FIGS. 2 and 3, the cell pushing shaft 3 of this embodiment has a shaft body 31, the small diameter end portion 32 provided at a front end of the shaft body 31, and the enlarged diameter portion 33 having the outer diameter larger than the outer diameter of the small diameter end portion 32. In addition, the cell pushing shaft 3 of this embodiment has an inner core 35, an inner core coating portion 36 encapsulating the inner core 35, and an outer layer 37 encapsulating the inner core coating portion 36. In the cell pushing shaft 3 of this embodiment, a front end of the outer layer 37 is positioned proximally from a front end of the inner core coating portion 36 at a predetermined length. The enlarged diameter portion 33 is formed of a front end portion of the outer layer 37.

It is preferable that the inner core 35 is rigid to some extent. Specifically, as the inner core 35, a metallic linear member or a linear member made of hard resin is suitable. A plastically deformable metallic bar-shaped member is especially preferable. As the bar-shaped member, both a solid member and a hollow member can be used. By using the metallic bar-shaped member plastically deformable as the inner core 35, it is possible to shape the front end portion of the shaft 3 and that of the living cell transplanting device 1 into a required configuration. As the metallic bar-shaped member, a metallic wire made of such as stainless steel is suitable. Annealed stainless steel is especially suitable as the metallic bar-shaped member.

As shown in FIG. 2, the front end of the small diameter end portion 32 (front end of the inner core coating portion 36) of the shaft 3 is formed hemispherically in such a way that the diameter of the front end of the small diameter end portion becomes gradually smaller toward the front end thereof. Therefore, it is possible to prevent an inner wall of a living body from being damaged in inserting the living cell transplanting device into the living body and removing it therefrom. The inner core coating portion 36 coats the entire inner core 35 including its front and rear ends.

As materials for forming the inner core coating portion 36, it is possible to use polyester, polyolefin (for example, polyethylene, polypropylene, ethylene-propylene copolymer), polyamide (for example, nylon 6, nylon 66), polyester (for example, polyethylene terephthalate), and fluororesin (for example, PTFE, ETFE).

As the materials for forming the inner core coating portion 36, those having flexibility may be used. It is possible to use synthetic rubber such as urethane rubber, silicone rubber, and butadiene rubber, natural rubber such as latex rubber, soft vinyl chloride, polyolefin (polyethylene, polypropylene, ethylene-propylene copolymer, ethylene-vinyl acetate copolymer, and mixture of polypropylene and polyethylene or polybutene), polyester (polyethylene terephthalate, polybutylene terephthalate), polyamide, elastomers such as polyolefin elastomers, polyamide elastomers, styrene elastomers (for example, styrene-butadiene-styrene copolymer, styrene-isoprene-styrene copolymer, and styrene-ethylene butylene-styrene copolymer), polyurethane, and thermoplastic polyurethane (thermoplastic polyether polyurethane and thermoplastic polyester polyurethane are preferable. Segmented thermoplastic polyether polyurethane having a soft segment part and a hard segment part is especially preferable. More specifically, as main components of the soft segment, polytetramethylene ether glycol, polyethylene glycol, and polypropylene glycol are preferable. As main components of the hard segment, 1,4-butanediol and the like are preferable). It is preferable to use rubber such as the silicone rubber or elastomers for forming the inner core coating portion. The silicone rubber is especially preferable. The silicone rubber having a 200% modulus of 30-90 kg/cm$^2$ is used. The silicone rubber having a 200% modulus of 40-60 kg/cm$^2$ is preferably used.

The outer layer 37 of this embodiment coats a side of the inner core coating portion 36 in such a way as to expose its front end portion and proximal end portion to the outside. The outer layer 37 may coat a rear end portion of the inner core coating portion 36. The inner core coating portion and the outer layer may me integrally formed. As materials for forming the outer layer 37, it is possible to use the materials which can be used for the inner core coating portion 36, as described previously. It is preferable that the outer layer 37 has a low sliding contact resistance to an inner surface of the flexible tube 2. From this point of view, fluororesin (for example, PTFE, ETFE) is suitable as materials for forming the outer layer 37.

The surface of the front end portion of the cell pushing shaft 3 and the inner surface of the front end portion of the tube 2 may be a surface to which cells can hardly adhere. By forming the above-described surface of the front end portion of the cell pushing shaft 3 and the above-described inner surface of the front end portion of the tube 2 in this way, adherence-caused cells which remain in the shaft and the tube is very small in the number thereof. It is possible to use oil such as silicone oil or vegetable oil administrable to living bodies for the surface to which cells can hardly adhere.

Figure 16:
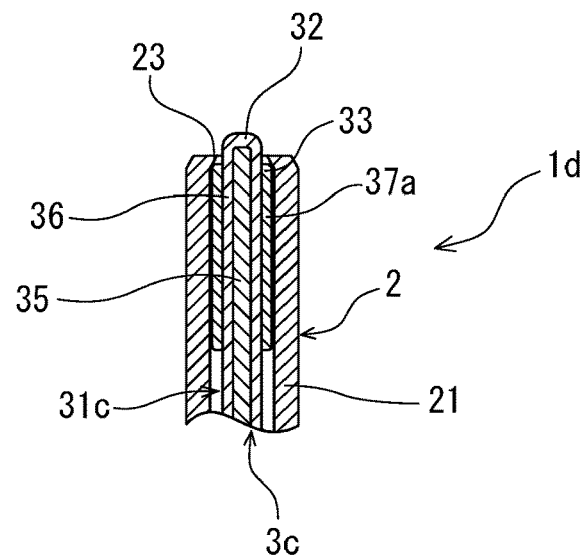
FIG. 16 is an enlarged longitudinal sectional view of a front end portion of a living cell transplanting device of another embodiment of the present invention.
Figure 17:
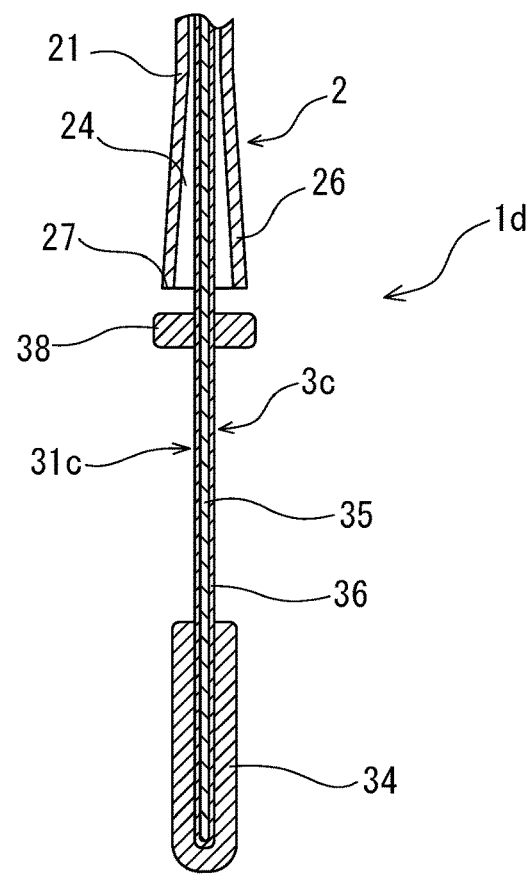
FIG. 17 is an enlarged longitudinal sectional view of a proximal part of the living cell transplanting device of another embodiment of the present invention.

In the living cell transplanting device 1 of this embodiment, the outer layer 37 is formed almost entirely on the shaft 3. By forming the outer layer 37 on the shaft 3, the shaft 3 has an operational stability, i.e., a favorable sliding contact operability in its longitudinal movement. But the construction of the living cell transplanting device of the present invention is not limited to that of the living cell transplanting device 1. For example, like a living cell transplanting device 1d shown in FIGS. 16 and 17, the living cell transplanting device of the present invention may have an outer layer 37a formed on only a front end part of a shaft 3c. In the shaft 3c of this embodiment, the outer layer 37a is formed on only the front end part of a shaft body 31c, whereas a part of the shaft 3c rearward from a rear end of the outer layer 37a is constructed of the inner core 35 and the inner core coating portion 36 and is thus smaller than the enlarged diameter portion 33 in the outer diameter thereof.

The cell pushing shaft 3 is set longer than the flexible tube 2 at a predetermined length. The entire length of the shaft 3 is 50 to 300 mm and preferably 100 to 250 mm. The outer diameter of the shaft 3 is 1 to 3 mm and preferably 1 to 2.5 mm.

The shaft 3 of this embodiment is provided with a tubular gripping portion 34 at its rear end portion. The gripping portion 34 is gripped in an operation of slidably moving the shaft.

The shaft 3 of this embodiment is provided with a regulation member 38 for regulating the projection length of the front end portion of the shaft at a portion of its proximal side. When the shaft 3 is pushed into the tube, the regulation member 38 is brought into contact with the rear end 27 of the tube 2 and thereby prevents the shaft from being pushed any further. By providing the shaft with the regulation member 38, it is possible to set the projected length of the front end portion of the shaft at the time of pushing the shaft 3 into the tube and prevent the front end portion thereof from excessively projecting. In addition, because an operator can recognize that it is necessary to push the shaft into the tube until the regulation member is brought into contact with the rear end of the tube, the operator can securely project the front end portion of the enlarged diameter portion of the shaft beyond the front end of the tube and thereby can prevent cells from remaining inside the tube.

As shown in FIG. 3, the regulation member 38 of this embodiment is a ring-shaped member capable of contacting the rear end surface of the rear end 27 of the tube 2. As materials for forming the regulation member 38, it is possible to preferably use the materials which have been described as the materials for forming the inner core coating portion 36.

In the living cell transplanting device (device for transplanting ovary tissues to beneath serosa of uterine tube) 1 of this embodiment, owing to the contact between the enlarged diameter portion 33 of the cell pushing shaft 3 and the reduced diameter front end open portion 23 of the flexible tube 2, the cell pushing shaft 3 inserted into the flexible tube 2 is prevented from advancing inside the flexible tube. As shown in FIG. 2, when the front end portion of the small diameter end portion 32 of the shaft 3 inserted into the flexible tube 2 projects beyond the reduced diameter front end open portion 23 of the flexible tube 2 with the enlarged diameter portion 33 of the shaft 3 in contact with the reduced diameter front end open portion 23 of the flexible tube 2, the shaft is prevented from being inserted into the flexible tube any further.

In this state, the front end portion of the small diameter end portion 32 of the shaft 3 is slightly projected beyond the reduced diameter front end open portion 23 of the flexible tube 2. The projected length of the small diameter end portion 32 of the shaft 3 with respect to the reduced diameter front end open portion 23 of the flexible tube 2 is preferably 0.2 to 5 mm and especially preferably 0.5 to 3 mm.

In the state in which the enlarged diameter portion 33 of the shaft 3 is in contact with the reduced diameter front end open portion 23 of the flexible tube 2, as shown in FIG. 3, the rear part of the shaft 3 is projected beyond the rear end 27 of the tube 2. In this state, the regulation member 38 of the shaft 3 is not in contact with the rear end 27 of the tube 2.

Figure 5:
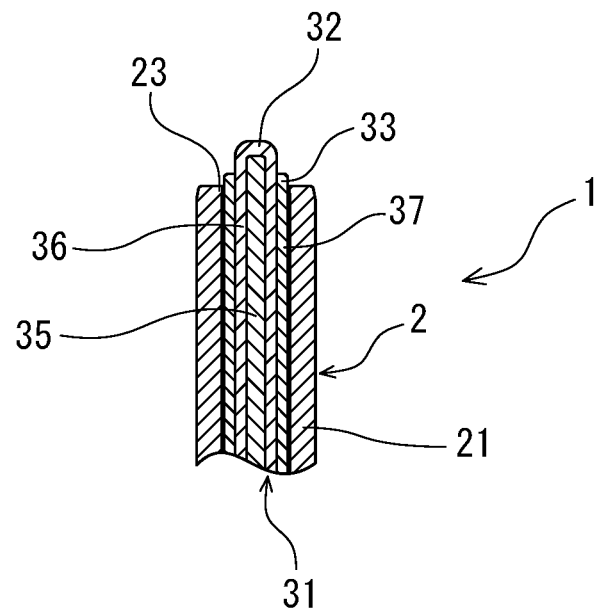
FIG. 5 is an explanatory drawing for explaining the action of the living cell transplanting device shown in FIG. 1.

When the cell pushing shaft 3 is pushed into the tube in the state in which the enlarged diameter portion 33 of the shaft 3 and the reduced diameter front end open portion 23 of the flexible tube 2 are in contact with each other, as shown in FIG. 5, the enlarged diameter portion 33 of the shaft 3 passes through the reduced diameter front end open portion with expanding the front end open portion 23 of the tube 2. Thereafter the front end of the enlarged diameter portion 33 projects beyond the reduced diameter front end open portion 23 of the flexible tube 2. After the front end of the enlarged diameter portion 33 projects beyond the reduced diameter front end open portion 23 of the flexible tube 2, the regulation member 38 of the shaft 3 is brought into contact with the rear end 27 of the tube 2. Thereby a further sliding contact movement of the shaft 3 toward the front end of the shaft 3 is prevented.

Figure 6:
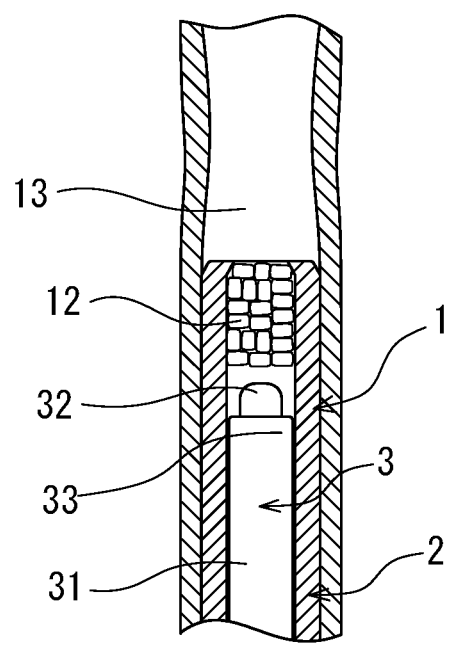
FIG. 6 is an explanatory drawing for explaining the action of the living cell transplanting device shown in FIG. 1.
Figure 7:
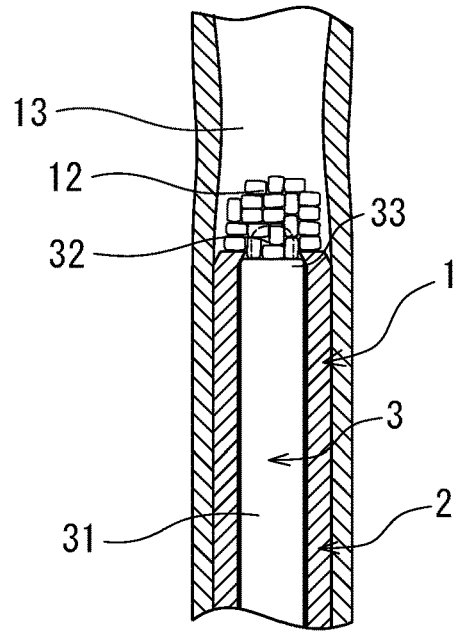
FIG. 7 is an explanatory drawing for explaining the action of the living cell transplanting device shown in FIG. 1.
Figure 8:
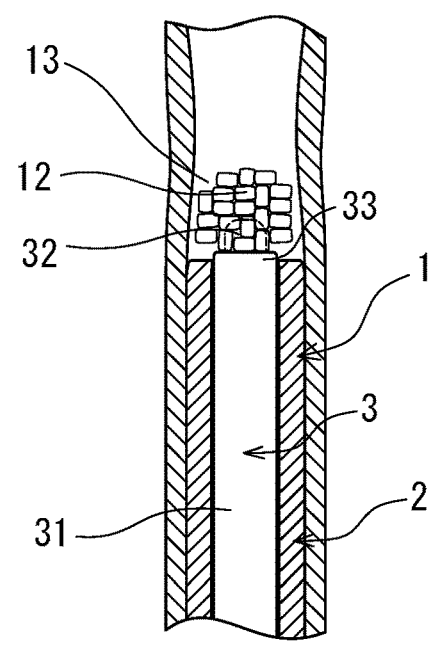
FIG. 8 is an explanatory drawing for explaining the action of the living cell transplanting device shown in FIG. 1.

The action of the living cell transplanting device 1 of the present invention is described below with reference to FIGS. 6 through 8.

After the ovary is laparoscopically removed from a patient, the removed ovarian tissue is cryopreserved. After the thawed ovarian tissue (ovarian cortex) is broken into small fragments of having a size of about 1 to 2 mm, the small fragments of ovarian tissue are cultured for 48 hours by using a PTEN inhibitor and a P13K activator to activate a P13K-Akt signal. After the culturing of the small fragments of the ovarian tissue finishes, the ovarian tissue are washed thoroughly to perform laparoscopic autologous ovarian transplantation. Initially, with the cell pushing shaft 3 being drawn slightly rearward, the living cell transplanting device 1 of the present invention having a cell accommodating portion formed inside the front end portion of the flexible tube 2 is prepared. Thereafter, if necessary, by using an applicator, a large number of the small fragments of the ovarian tissue are filled into the cell accommodating portion formed inside the front end portion of the tube 2 from the front end opening portion of the flexible tube 2.

After the neighborhood of the uterine tube is laparoscopically partially incised, the front end portion of the living cell transplanting device 1 of the present invention prepared in the above-described manner is disposed at a portion 13 disposed between the serosa of the uterine tube and the uterine tube which have appeared by the incision. By slidably moving the shaft 3 toward the front end of the tube, the small fragments of the ovarian tissue filled in the tube 2 are transplanted little by little to the portion 13 disposed between the serosa of the uterine tube and the uterine tube. As the shaft 3 moves toward the front end of the tube, as shown in FIG. 7, the regulation member 38 of the shaft 3 is brought into contact with the rear end 27 of the tube 2. Thereby it is possible to confirm that most of the small fragments of the ovarian tissue inside the tube 2 has been transplanted. As shown in FIG. 8, by further pushing of the shaft 3, the enlarged diameter portion 33 of the shaft 3 passes the reduced diameter front end open portion 23 of the tube 2 with the enlarged diameter portion expanding the reduced diameter front end open portion 23. Thereafter the front end of the enlarged diameter portion 33 projects beyond the reduced diameter front end open portion 23 of the flexible tube 2. Thereby almost all of the small fragments of the ovarian tissue inside the shaft 2 are transplanted to the portion 13 disposed between the serosa of the uterine tube and the uterine tube.

Figure 9:
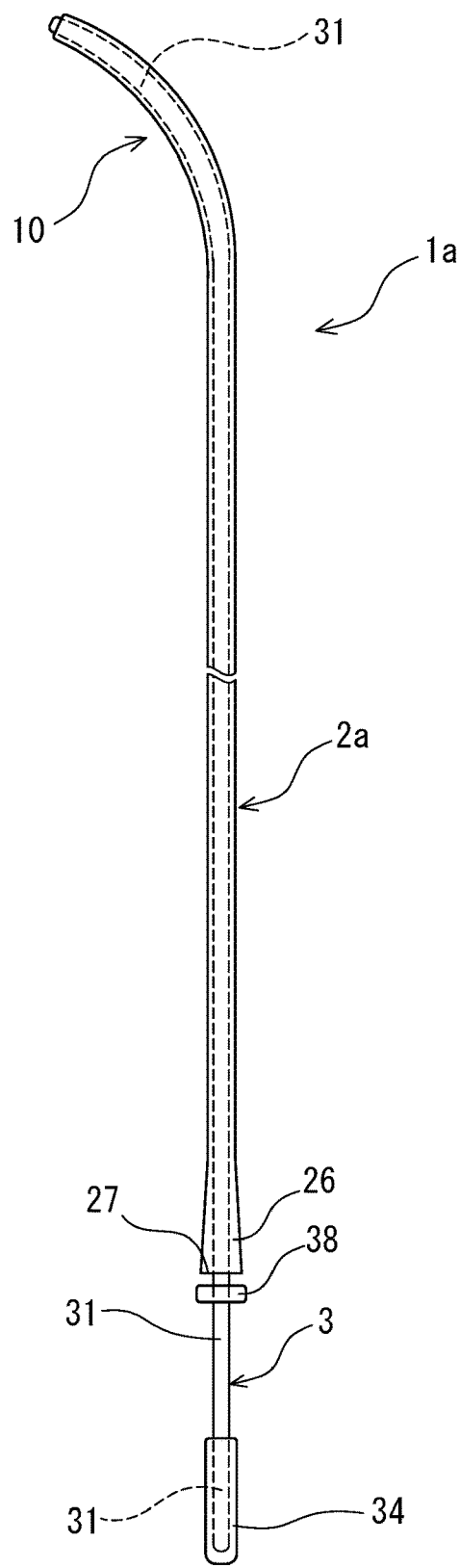
FIG. 9 is a front view of a living cell transplanting device of another embodiment of the present invention.

The living cell transplanting device of the present invention may have a curved front region 10 like a living cell transplanting device 1a shown in FIG. 9. The curved front region 10 can be formed by shaping the front end portion of the cell pushing shaft 3 into a curved configuration to allow a flexible tube 2a to follow the formed curved configuration of the cell pushing shaft. It is also possible to form the curved front region by shaping the front end portion of the cell pushing shaft 3 and that of the flexible tube into the curved configuration respectively. It is preferable to form the curved front region 10 by curving a portion of the living cell transplanting device 1a located 20 to 100 mm from the front end thereof.

Figure 10:
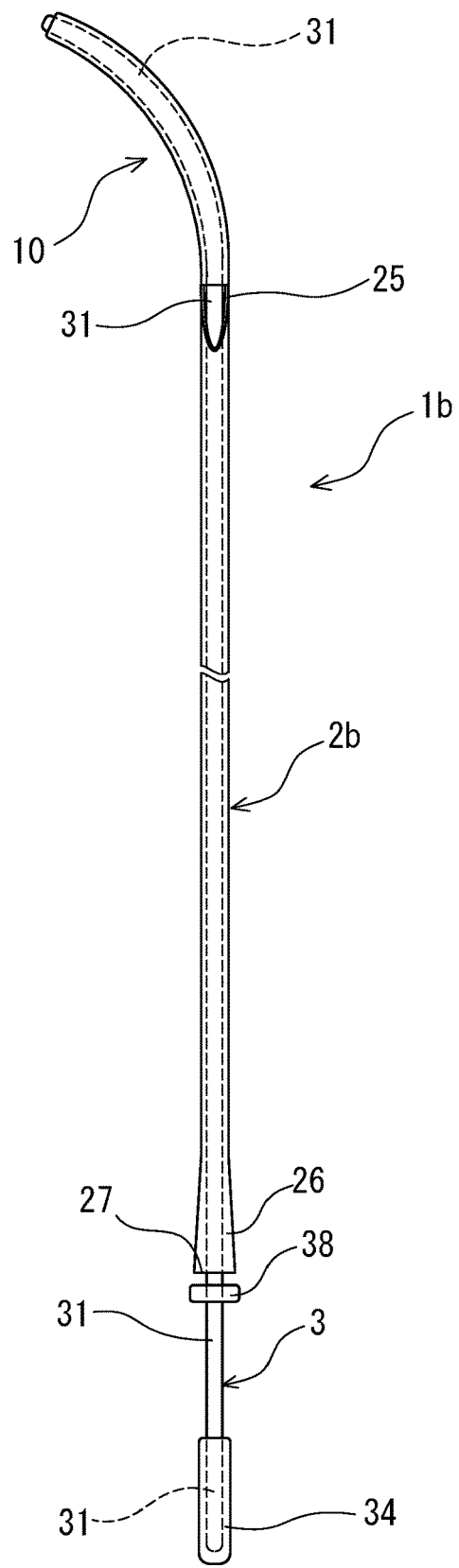
FIG. 10 is a front view of a living cell transplanting device of still another embodiment of the present invention.
Figure 13:
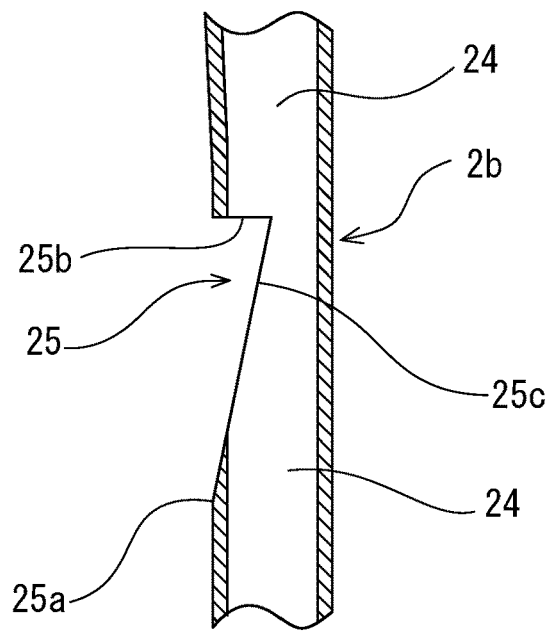
FIG. 13 is an enlarged longitudinal sectional view for explaining the side opening of the flexible tube for use in the living cell transplanting device shown in FIG. 10.

The living cell transplanting device of the present invention may have a living cell-filling side opening 25 as the in the case of a living cell transplanting device 1b shown in FIG. 10. It is preferable to form the living cell-filling side opening 25 in a front side of a flexible tube 2b.

As shown in FIGS. 11 through 15, it is preferable that the living cell-filling side opening 25 becomes gradually deeper toward a front end of the flexible tube 2b. In the living cell transplanting device of this embodiment, the side opening 25 has a starting edge 25a positioned at a proximal end side thereof, a tilted opening surface 25c extended from the starting edge 25a toward the axis of the flexible tube 2b and the front end thereof, and an erect opening surface 25b positioned at a front end of the tilted opening surface 25c. The open width of the side opening 25 becomes gradually larger from the starting edge 25a toward the erect opening surface 25b. The depth of the side opening 25 becomes gradually larger from the starting edge 25a toward the erect opening surface 25b.

Figure 14:
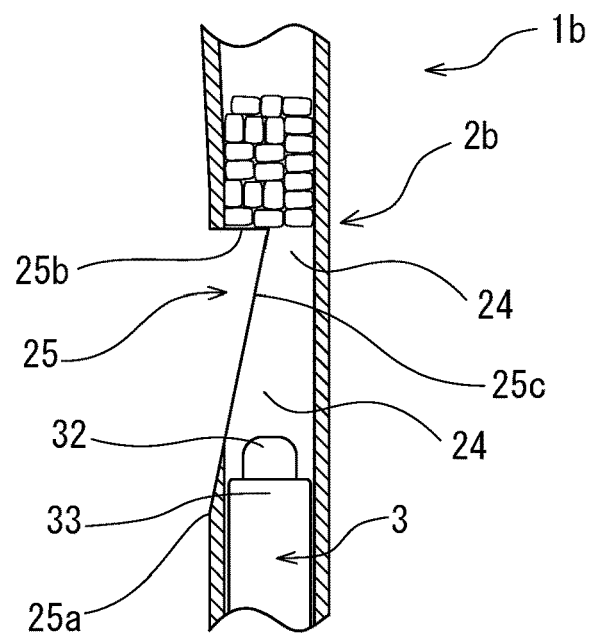
FIG. 14 is an explanatory drawing for explaining the action of the living cell transplanting device shown in FIG. 10.
Figure 15:
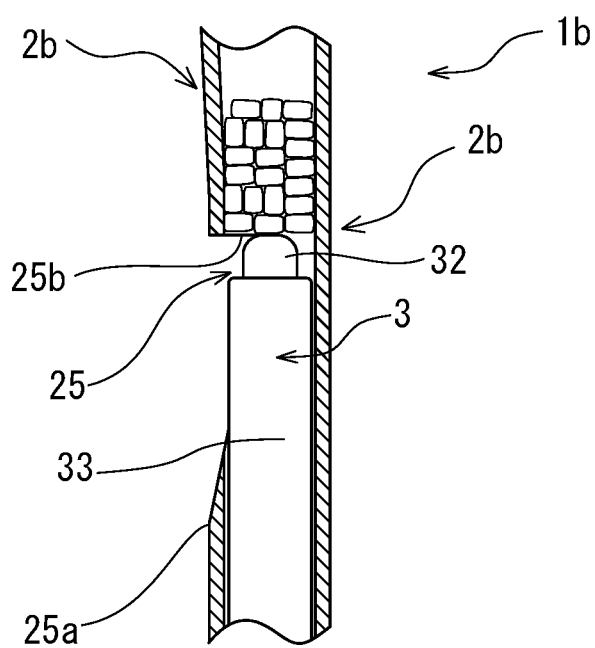
FIG. 15 is an explanatory drawing for explaining the action of the living cell transplanting device shown in FIG. 10.

The length of the side opening 25 in its axial direction is preferably 5 to 15 mm and especially preferably 7 to 12 mm. It is preferable that the dimension of the side opening (opening) 25 at its maximum width is equal to or close to the inner diameter of the flexible tube 2b. It is preferable that the erect surface 25b is orthogonal to the central axis of the flexible tube 2b. By providing the side opening 25 with the above-described form, as shown in FIG. 14, the living cells can be securely and easily filled into the front side of the flexible tube 2b from the side opening 25. In addition, as shown in FIG. 15, it is possible to insert the living cell transplanting device 1b into the living body in a state where the small diameter end portion 32 of the cell pushing shaft 3 is positioned in the vicinity of the front end of the side opening 25. Thus, it is possible to prevent the flexible tube 2 from kinking at the side opening 25 in an operation of inserting into the living body.

The length of the side opening 25 in its axial direction is preferably 5 to 15 mm and especially preferably 7 to 12 mm. It is preferable that the dimension of the side opening (opening) 25 at its maximum width is equal to or close to the inner diameter of the flexible tube 2b. It is preferable that the erect surface 25b is orthogonal to the central axis of the flexible tube 2b. By providing the side opening 25 with the above-described form, as shown in FIG. 14, the living cells can be securely and easily filled into the front side of the flexible tube 2b from the side opening 25. In addition, as shown in FIG. 15, it is possible to insert the living cell transplanting device 1b into the living body in a state where a front portion of the of the cell pushing shaft 3 is positioned in the front end of the side opening 25. Thus, it is possible to prevent the front portion of the flexible tube 2b from kinking at the side opening 25 in an operation of inserting the living cell transplanting device 1b into the living body.

As with the above-described living cell transplanting device 1a, the living cell transplanting device 1b shown in FIG. 10 has the curved front region 10. The living cell transplanting device 1b of this embodiment has the living cell-filling side opening 25 at a front end portion of an uncurved front region (straight part) positioned proximally from a proximal end of the curved front region 10. The opening 25 may be formed in the curved front region 10 at its front end portion or proximal end portion.

In this embodiment, as shown in FIG. 12, the side opening 25 is formed at a position of a side of the curved front region 10 in its curved direction. In other words, as shown in FIG. 12, the side opening 25 is formed at a position not on an inner side or an outer side of the curved front region 10 in its curved direction, but at a position of a side surface of the curved front region 10 in its curved direction. Thus, when the flexible tube 2b is placed on a flat surface of a working table or the like in such a way that the curved front region contacts the flat surface, the side opening 25 faces upward. Thereby it is easy to perform a cell-filling operation to the side opening.

In a case where the flexible tube not having the curved front region is provided with the living cell-filling side opening, it is preferable to form the side opening in the vicinity of the front end of the flexible tube.

The living cell-filling side opening to be formed in the living cell transplanting device of the present invention may have a form of a side opening 85 which a living cell transplanting device 1c shown in FIGS. 18 through 22 has. In this embodiment, it is also preferable to form the side opening 85 in the front region of a flexible tube 2c.

As shown in FIGS. 18 through 22, the living cell-filling side opening 85 of this embodiment becomes gradually deeper toward the proximal end of a flexible tube 2c. The side opening 85 has a starting edge 85a positioned at a front end side thereof, a tilted opening surface 85c extended from the starting edge 85a toward the axis of the flexible tube 2c and the proximal end thereof, and an erect opening surface 85b positioned at a terminal of the tilted opening surface 85c. The open width of the side opening 85 becomes gradually larger from the starting edge 85a toward the erect opening surface 85b. The depth of the side opening 85 becomes gradually larger from the starting edge 85a toward the erect opening surface 85b.

Figure 22:
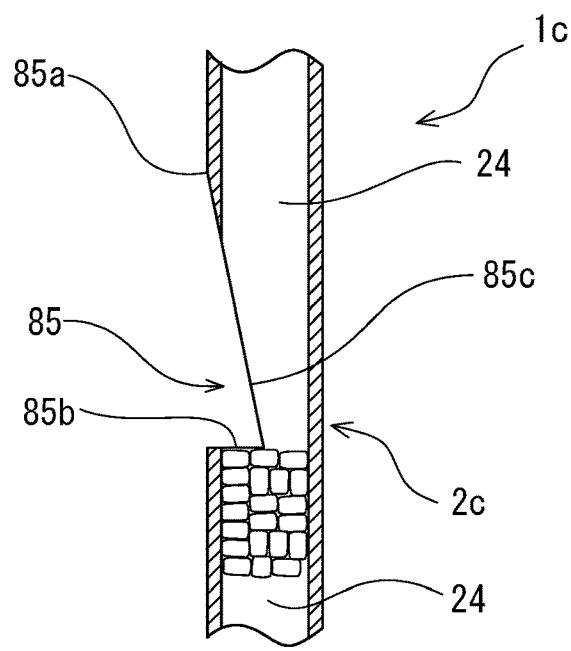
FIG. 22 is an explanatory drawing for explaining the action of the living cell transplanting device shown in FIG. 18.

The length of the side opening 85 in its axial direction is preferably 5 to 15 mm and especially preferably 7 to 12 mm. It is preferable that the dimension of the side opening (opening) 85 at its maximum width is equal to or close to the inner diameter of the flexible tube 2c. It is preferable that the erect surface 85b is orthogonal to the central axis of the flexible tube 2c. By providing the side opening 85 with the above-described form, as shown in FIG. 22, the living cells can be securely and easily filled into the proximal end side of the flexible tube 2c from the side opening 85.

Figure 18:
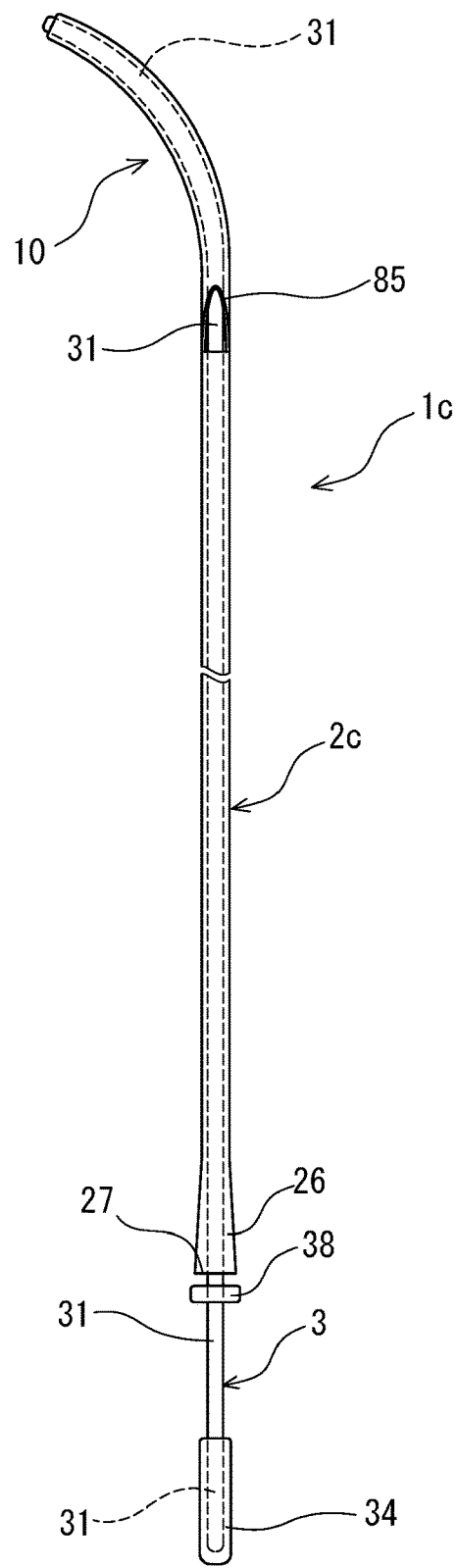
FIG. 18 is a front view of a living cell transplanting device of still another embodiment of the present invention.
Figure 19:
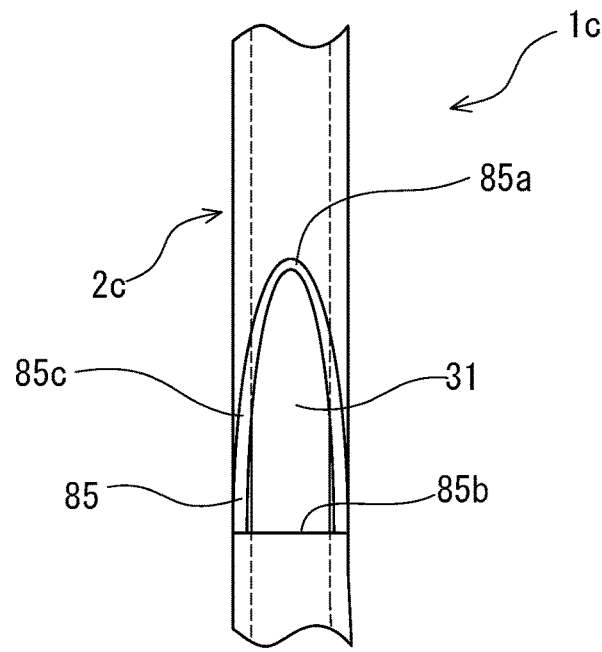
FIG. 19 is an enlarged front view of the vicinity of a side opening of the living cell transplanting device shown in FIG. 18.
Figure 20:
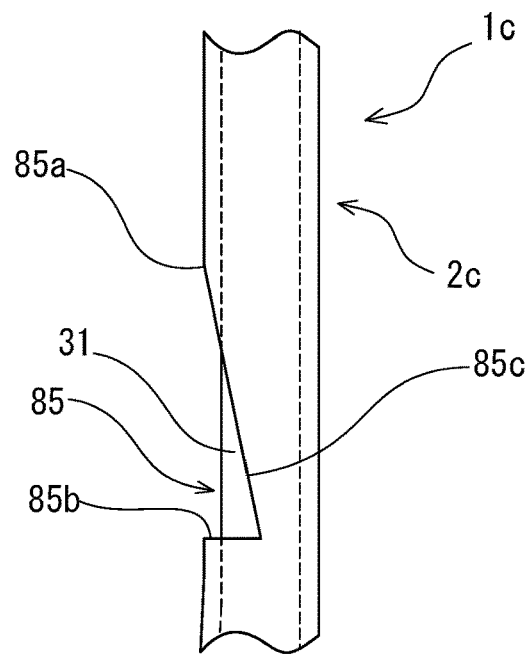
FIG. 20 is an enlarged right side view of the vicinity of the side opening of the living cell transplanting device shown in FIG. 18.
Figure 21:
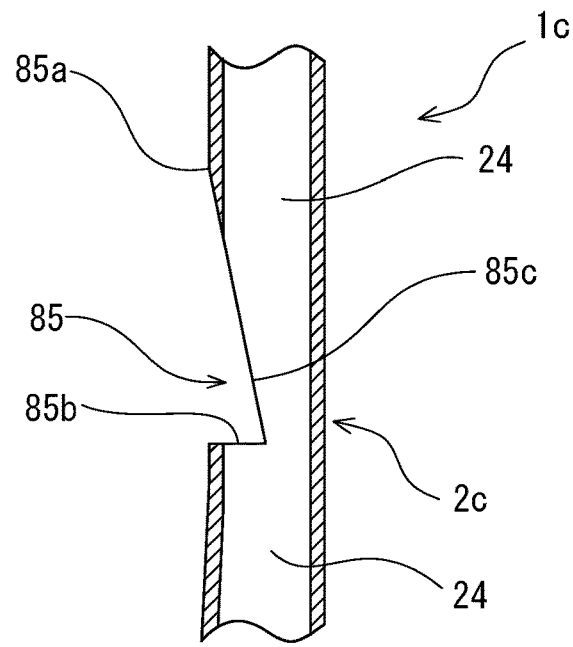
FIG. 21 is an enlarged longitudinal sectional view for explaining the side opening of the flexible tube for use in the living cell transplanting device shown in FIG. 18.

As with the above-described living cell transplanting device 1b, as shown in FIG. 18, the living cell transplanting device 1c has the curved front region 10. The living cell transplanting device 1c of this embodiment has the living cell-filling side opening 85 at a front end portion of an uncurved front region (straight part) positioned proximally from the proximal end of the curved front region 10. The opening 85 may be formed in the curved front region 10 at its front end portion or proximal end portion.

As shown in FIG. 18, in the living cell transplanting device 1c of this embodiment, the side opening 85 is also formed at a position of a side of the curved front region 10 in its curved direction. In other words, as shown in FIG. 18, the side opening 85 is formed at a position not on an inner side or an outer side of the curved front region 10 in its curved direction, but at a position of a side surface of the curved front region 10 in its curved direction. Thus, when the flexible tube 2c is placed on a flat surface of a working table or the like in such a way that the curved front region contacts the flat surface, the side opening 85 faces upward. Thereby it is easy to perform a cell-filling operation to the side opening.

In a case where the flexible tube not having the curved front region is provided with the living cell-filling side opening, it is preferable to form the side opening in the vicinity of the front end of the flexible tube.

INDUSTRIAL APPLICABILITY

The living cell transplanting device of the present invention has the following construction:

(1) A living cell transplanting device comprising a flexible tube capable of accommodating living cells and a cell pushing shaft inserted into said flexible tube;

wherein said flexible tube has a lumen penetrating therethrough from a front end thereof to a rear end thereof and a reduced diameter front end open portion;

said cell pushing shaft has a small diameter end portion having a diameter smaller than said reduced diameter front end open portion of said flexible tube and an enlarged diameter portion having an outer diameter larger than said small diameter end portion and said reduced diameter front end open portion and a little smaller than an inner diameter of said flexible tube, wherein a front end of said enlarged diameter portion is close to said small diameter end portion and located at a position rearward from said small diameter end portion; and owing to contact between said enlarged diameter portion of said cell pushing shaft and said reduced diameter front end open portion of said flexible tube, a progress of said cell pushing shaft inserted into said flexible tube is regulated; and by pushing said cell pushing shaft into said flexible tube after said contact between said enlarged diameter portion and said reduced diameter front end open portion finishes, said enlarged diameter portion of said shaft passes through said reduced diameter front end open portion with expanding said reduced diameter front end open portion of said tube and is capable of projecting beyond said reduced diameter front end open portion of said flexible tube.

According to the living cell transplanting device of the present invention, after the living cells, for example, a large number of small fragments of the ovary is filled into the flexible tube, the front end portion of the living cell transplanting device is disposed at the portion to which the living cells are to be transplanted, for example, the portion between the serosa of the uterine tube and the uterine tube with the front end portion of the shaft in contact with or close to the portion where the living cells have been filled. Thereafter the shaft is advanced. Thereby the living cells can be transplanted to the portion to which the living cells are to be transplanted. The operator can easily recognize that owing to the advance of the shaft, the enlarged diameter portion of the shaft has been brought into contact with the reduced diameter front end open portion of the tube and that most of the filled cells have been discharged from the transplanting device. By further pushing the shaft into the tube, the living cells which have remained inside the tube is pushed out of the tube and transplanted to the portion to which the living cells are to be transplanted. The resistance to the pushing of the shaft allows the operator to recognize that the living cells inside the tube can be securely pushed out of the tube and that the operator is performing an operation of pushing the remaining living cells out of the tube. Thereby it is possible to successfully transplant the living cells to the intended the portion to which the living cells are to be transplanted.

The above-described embodiments may be carried out as described below.

(2) A living cell transplanting device according to the above (1), wherein inner and outer diameters of said reduced diameter front end open portion become smaller in a tapered shape toward a front end thereof.

(3) A living cell transplanting device according to the above (1) or (2), wherein said cell pushing shaft has an inner core formed by a plastically deformable metallic bar-shaped member.

(4) A living cell transplanting device according to any one of the above (1) through (3), wherein said cell pushing shaft has a regulation member for regulating a projection length of a front end portion thereof; said regulation member being brought into contact with said rear end of said flexible tube after said enlarged diameter portion projects beyond said reduced diameter front end open portion of said flexible tube.

(5) A living cell transplanting device according to any one of the above (1) through (4), wherein said living cell transplanting device has a curved front region.

(6) A living cell transplanting device according to any one of the above (1) through (5), wherein said flexible tube has a living cell-filling side opening provided on a side surface of a front side of said tube.

(7) A living cell transplanting device according to any one of the above (1) through (4), having a curved front region, wherein said flexible tube has a living cell-filling side opening provided on a side surface of a front side of said tube, and said side opening is formed at a position located at a side of said curved front region in a curved direction thereof.

(8) A living cell transplanting device according to any one of the above (1) through (7), being used to transplant a large number of small fragments of a living tissue.

(9) A living cell transplanting device according to any one of the above (1) through (8), being used to transplant small fragments of an ovary to a portion disposed between a serosa of a uterine tube and said uterine tube.

Figure 23:
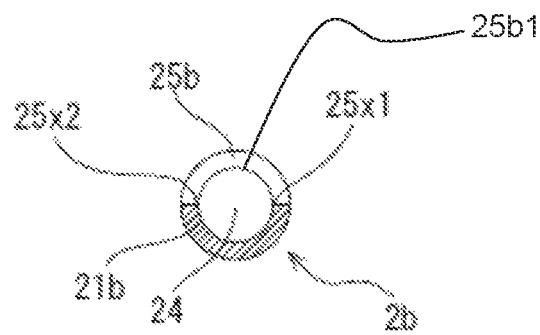
FIG. 23 is a sectional view of the flexible tube, seen from A-A line in FIG. 11.

With respect to the side opening 25, the side opening faces its peripheral of the tube. The tilted opening surface 25c is formed with a pair of quarter-elliptical tilted edges (25c1, 25c2) that extend from the starting edge 25a toward the erect opening surface 25b as the tilted edges curve. The erect opening surface 25b is shown in FIG. 23, which is a sectional view seen from A-A line in FIG. 11. The inner peripheral of the erect opening surface 25b at its proximal end is in an arc shape, which is termed as an arc-shaped edge 25b1. The arc-shaped edge 25b1 has the same curve as the inner peripheral of the lumen has in this embodiment. The arc-shaped edge extends (or curves) from one end 25x1 at the right and the other end 25x2 at the left. FIG. 23 shows that the arc-shape edge extends 180 degrees around the central axis of the tube. The extending degrees might be larger or smaller than 180 degrees depending on its design purpose.

Figure 24:
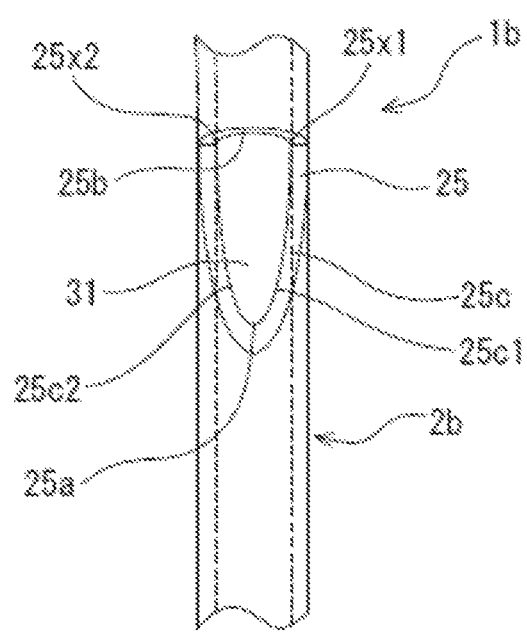
FIG. 24 is a perspective view of the side opening.

As shown in FIG. 24, one of the tilted edges (25c1) at right connects to the one end (25x1) and the other of the titled edges (25c2) at left connects to the other end (25x2) of said arc-shaped edge. It is noted that the actual shape of the side opening 25 is formed with the arc-shaped edge 25b1 and the pair of the tilted edges 25c1 and 25c2. The width of the side opening 25 is denoted with Dp in FIG. 12, and is determined by the pair of the titled edges, which is measured in a direction parallel to a line connecting these ends (25x1, 25x2). The depth of the arc-shaped edge is equal to about half the inner diameter of the lumen. The length of the tilted opening surface is denoted with Lg in FIG. 11. The length is determined in a direction parallel to the central axis of the lumen. In the drawing, the length is measured from the starting edge 25a to the erect opening surface 25b. In this invention, the tilted opening surface 25c and the erect opening surface 25b may be respectively termed as a first opening portion and a second opening portion. In the embodiment, a single side opening is present. In the light of the invention, two or more of side openings may be provided.

The invention claimed is:

1. A living cell transplanting, device comprising
a flexible tube capable of accommodating living cells and
a cell pushing shaft slidably inserted into said flexible tube;
wherein said flexible tube has a lumen penetrating therethrough from a front end thereof to a rear end thereof and a front end open portion with an inner diameter decreasing toward said front end thereof;
said cell pushing shaft has an end portion having an outer diameter smaller than an inner diameter of said front end open portion of said flexible tube and an enlarged diameter portion having an outer diameter larger than said outer diameter of said portion and said inner diameter of said front end open portion and a smaller than an inner diameter of said flexible tube,
wherein a front end of said enlarged diameter portion is close to said end portion and located at a position rearward from said small diameter end portion;
said enlarged diameter portion of said cell pushing shaft is contactable with said front end open portion of said flexible tube, said enlarged diameter portion of said shaft passes through said front end open portion with expanding said front end open portion of said flexible tube and is capable of projecting beyond said front end open portion of said flexible tube by pushing said cell pushing shaft,
said flexible tube has a living cell-filling side opening provided at a front side position of said flexible tube wherein said front side position is closer to said front end of said flexible tube than to said rear end and is distant from said front end such that a living cell storage portion is formed in said lumen, extending from said front side position toward said front end of said flexible tube to store said living cell inserted from said living cell-filling side opening, and said living cell-filling side opening communicates to said front end open portion of said flexible tube through said lumen of said flexible tube to push out said living cells, which are stored in said living cell storage portion, from said front end open portion by said cell pushing shaft,
said living cell-filling side opening has a first opening portion facing a side of said flexible tube and a second opening portion facing said rear end of said flexible tube,
said second opening portion has an arc-shaped edge, which is in an arc shape extending from one end to the other end,
said first opening portion has a semi-elliptical edge having a starting edge positioned at a proximal end side thereof, said semi-elliptical edge has a pair of quarter-elliptical tilted edges that extend from said starting edge toward said second opening portion as curving wherein one of the tilted edges connects to the one end and the other of the titled edges connects to the other end of said arc-shaped edge, and the tilted edges are arranged inclined with respect to a central axis of said flexible tube, a width of said first opening portion surrounded by said quarter-elliptical edges becomes gradually larger from said starting edge toward said second opening portion wherein the width of said first opening portion is determined in a direction parallel to a line connecting the one end and the other end of the said arc-shaped edge, and said second opening portion is orthogonal to said central axis of said flexible tube, a depth of said arc-shaped edge of said second opening portion, which is measured orthogonal to the central axis of said flexible tube, is about half said inner diameter of said lumen of said flexible tube.

2. A living cell transplanting device according to claim 1, wherein inner and outer diameters of said reduced diameter front end open portion become smaller in a tapered shape toward a front end thereof.

3. A living cell transplanting device according to claim 1, wherein said cell pushing shaft has an inner core formed by a plastically deformable metallic bar-shaped member.

4. A living cell transplanting device according to claim 1, wherein said cell pushing shaft has a regulation member; said regulation member contacts with said rear end of said flexible tube when said enlarged diameter portion projects beyond said reduced diameter front end open portion of said flexible tube.

5. A living cell transplanting device according to claim 1, wherein said living cell transplanting device has a curved front region.

6. A living cell transplanting device according to claim 1, wherein said living cell transplanting device has a curved front region, said living cell-filling side opening is provided on a side surface of the front side position of said tube, and said side opening is formed at a position located at a side of said curved front region in a curved direction thereof.

7. A living cell transplanting device according to claim 1, being used to transplant fragments of a living tissue.

8. A living cell transplanting device according to claim 1, being used to transplant small fragments of an ovary to a portion disposed between a serosa of a uterine tube and said uterine tube.

9. A living cell transplanting device according to claim 1, wherein a dimension of said side opening at its maximum width is equal to or close to an inner diameter of said flexible tube.

* * * * *